United States Patent [19]
Sablotsky et al.

[11] Patent Number: 5,300,291
[45] Date of Patent: Apr. 5, 1994

[54] METHOD AND DEVICE FOR THE RELEASE OF DRUGS TO THE SKIN

[75] Inventors: Steven Sablotsky, Miami; Joseph A. Gentile, Plantation, both of Fla.

[73] Assignee: Noven Pharmaceuticals, Inc., Miami, Fla.

[21] Appl. No.: 671,709

[22] Filed: Apr. 2, 1991

Related U.S. Application Data

[63] Continuation-in-part of Ser. No. 295,847, Jan. 11, 1989, Pat. No. 4,994,267, which is a continuation-in-part of Ser. No. 164,482, Mar. 4, 1988, Pat. No. 4,814,168.

[51] Int. Cl.$^5$ ............................................. A61K 31/74
[52] U.S. Cl. .............................. 424/78.18; 424/485; 424/484; 424/448
[58] Field of Search ............... 424/78, 449, 448, 447, 424/484, 485, 486, 78.18; 524/504

[56] References Cited

U.S. PATENT DOCUMENTS

| | | | |
|---|---|---|---|
| 3,948,262 | 4/1976 | Zaffaroni | 424/449 |
| 4,144,317 | 3/1979 | Higuchi et al. | 424/435 |
| 4,379,454 | 4/1983 | Campbell et al. | 604/897 |
| 4,391,797 | 7/1983 | Folkman et al. | 424/425 |
| 4,421,737 | 12/1983 | Ito et al. | 424/449 |
| 4,624,665 | 11/1986 | Nuwayser et al. | 424/78 |
| 4,661,099 | 4/1987 | von Bittera et al. | 428/261 |
| 4,751,087 | 6/1988 | Wick | 424/449 |
| 4,814,168 | 3/1989 | Sablotsky | 514/182 |
| 4,994,267 | 2/1991 | Sablotsky | 424/78 |

FOREIGN PATENT DOCUMENTS

| | | |
|---|---|---|
| 62-230716 | 3/1986 | Japan . |
| 62-230717 | 3/1986 | Japan . |
| 62-230717 | 10/1987 | Japan . |
| 1126849 | 9/1968 | United Kingdom . |
| 2073588 | 10/1981 | United Kingdom . |

Primary Examiner—Thurman K. Page
Assistant Examiner—Leon R. Horne
Attorney, Agent, or Firm—Foley & Lardner

[57] ABSTRACT

A method of increasing the adhesiveness of a shaped pressure sensitive adhesive, comprising adding an adhesiveness and drug release increasing amount of a clay to said adhesive prior to casting of the adhesive.

A dermal composition comprising a drug, a pressure sensitive adhesive, an adhesiveness increasing amount of a clay and a solvent.

A dermal composition comprising a drug, a multipolymer of ethylene vinyl acetate, an acrylic polymer, a natural or synthetic rubber and a clay, along with optional ingredients known for use in transdermal drug delivery systems.

36 Claims, 1 Drawing Sheet

FIG. 1

KAOLINITE

ALUMINUM SILICON

FIG. 2

MONTMORILLONITE

← CATIONS

← WATER

FIG. 3

OCTAHEDRAL

FIG. 4

TETRAHEDRAL

METHOD AND DEVICE FOR THE RELEASE OF DRUGS TO THE SKIN

CROSS-REFERENCE TO RELATED APPLICATION

This application is a continuation-in-part of U.S. patent application Ser. No., 07/295,847 filed Jan. 11, 1989, which in turn is a continuation-in-part of U.S. patent application Ser. No. 164,482, filed Mar. 4, 1988, now U.S. Pat. No. 4,814,168 granted Mar. 21, 1989, which application and patent are incorporated herein by reference. The application and patent are assigned to Noven Pharmaceuticals, Inc. of Miami, Fla.

BACKGROUND OF THE INVENTION

This invention relates to a method and device for delivering drugs to the body through intact skin and more particularly to such devices which incorporate a pressure sensitive adhesive and even more particularly to such devices having at least two phases, a phase formed of a polymer matrix having limited water solubility and, in admixture, an interpenetrating phase of drug, polymer, liquid such as a solvent or a solid, or one or more of the foregoing.

Devices that deliver drugs through intact skin, namely the epidermis, for absorption into the body and the systemic circulatory system have been known for some time. Such devices can be referred to as transdermal drug delivery devices or dermal compositions.

The purpose of such devices is to dispense a drug at a controlled, and if desired, constant rate by presenting the drug in an efficient manner, with the minimum degradation or complications from the drug or from failure to comply with the therapeutic regimen.

A typical prior art system using a polymer matrix involves diffusion of the drug at a controlled rate through the polymer. However, such systems, as a result of the need for a rate limiting means, are more complicated to manufacture. For example, U.S. Pat. Nos. 3,948,262, 4,144,317 and 4,379,454 assigned to Alza and Ciba relate to transdermal drug delivery systems. The controlled delivery devices of those patents are structurally distinct, operate differently and accordingly, do not provide the delivery kinetics obtained with the system of this invention.

It is known to deliver drugs from natural or synthetic rubbers, or from acrylic polymers or from ethylene vinyl acetate, the drugs passing from the polymers by diffusion. It is also known from related application U.S. Pat. No. 4,814,168 to use a multipolymer adhesive incorporating a drug. It is further known from related application Ser. No. 295,847 filed Jan. 11, 1989, now U.S. Pat. No. 4,994,267 to use a combination of a rubber, acrylic and ethylene vinyl acetate polymers as the multipolymer.

It is known to use fillers in transdermal drug delivery devices U.S. Pat. No. 4,421,737 refers to fillers used traditionally for ordinary adhesive tapes in connection with a nitroglycerin transdermal drug delivery device. That patent further indicates that "kaolin and clay" are fillers with mild acidity which can be used to absorb nitroglycerin to regulate nitroglycerin release. The patent indicates that the use of the filler is optional, but that when the filler is used it can be used in amounts up to two times the amount by weight of the adhesive, with the drug nitroglycerin representing 1 to 10% by weight of the "whole amount of the adhesive." The preferred range of filler was indicated to be from about 0 to 1.2 times the weight of the adhesive, with the nitroglycerin representing 1 to 10% of "the whole amount of the adhesive." Thus in U.S. Pat. No. 4,421,737 the drug nitroglycerin was a minor component of the system. Since nitroglycerin acts as a plasticizer for the adhesive, increasing amounts lead to increasing tackiness and eventually liquidity. Thus the clay functions as an absorbent for the liquid nitroglycerin to decrease the liquifying effect of the nitroglycerin.

Of increasing interest are transdermal drug delivery devices in which the drug is incorporated into a pressure sensitive adhesive, which serves not only to carry the drug, but to attach the device to the skin.

The introduction of a drug into a pressure sensitive adhesive, as distinct from carrying the drug in a separate structure of the device, results in a variety of delivery and adhesion problems.

Adhesion problems vary with, among other things, the nature of the polymers forming the pressure sensitive adhesive, the type and amount of drug, the type and amount of other ingredients in the system and the conditions of use.

The transdermal device must be strong enough to adhere to the wearer for a specified length of time. Otherwise the individual will not receive the prescribed amount of medication However, if the adhesion is too strong, the wearer may encounter mechanical irritation upon removal. Adhesiveness of any device varies with time on the skin. Initial adhesion may be adequate However, when the wearer begins to perspire, adhesiveness may be reduced.

Various attempts have been made to overcome the delivery deficiency problems of the prior art transdermal systems. Gels formed of crosslinked hydrophilic polyacrylamide and polyvinylpyrrolidone polymers have been used as carriers However, the single phase gel compositions did not lead to systems having acceptable release properties because the duration of release depends upon the density of the gel, which property is difficult to control with standard manufacturing techniques. U.S. Pat. No. 4,391,797 attempted to solve such problems, particular for implants and drugs having a molecular weight of at least 1000 by combining a relatively water insoluble polymer matrix such as ethylene vinyl acetate copolymer with a swellable, hydrophylic drug having a molecular weight of at least 1000.

It is also known that the inclusion of a solid in an ethylene vinyl acetate polymer can result in pore formation. See Grace U.K. Patent Specification No. 1,126,849.

One aspect of this invention is based on the finding that it is not at all necessary or desirable to control the release of the drug from the polymer, for example, by a rate limiting membrane, so that there is a uniform delivery rate per unit time. Rather, improved results are obtained when the drug is delivered to the skin as rapidly as practicable, namely where the rate of release is not constant, but decreases over time. This more rapid release in fact may result in improved delivery of the drug to the body system as shown by blood levels of drug having a more narrow therapeutic range and smaller peak to trough ratios.

Another aspect of this invention is the finding that the addition of a clay to a transdermal drug delivery device, namely a dermal composition, increases the adhesiveness of such device. Specifically, one aspect of this invention is the addition of an adhesiveness increasing amount of a clay to a mixture of a drug and a pressure sensitive adhesive, particularly an adhesive containing a solvent for one or more of the components of the composition.

This invention also permits more rapid release of the drug while increasing adhesiveness.

The clay is used in an adhesiveness increasing amount, which in any event is a minor amount based on the total weight of the composition. The term "a minor amount" used here means less than about 50% and preferably less than 20% and more preferably less than about 10% or even about 5% by weight of the total composition. Use of higher amounts of clay results in an unacceptable retardation in the release rate of the drug. Surprisingly, it has been found that the addition of a clay increases the adhesiveness of a tacky polymer, despite previous reports that clay reduces cohesiveness and impliedly adhesiveness.

SUMMARY OF THE INVENTION

This invention resides in the discovery that drugs may be delivered over prolonged periods of time in a highly effective manner using polymer matrixes of limited aqueous and biological fluid solubility and having at least two phases.

This invention relates to a method of increasing the adhesiveness of a shaped pressure sensitive adhesive. This increase in adhesiveness is achieved by adding an adhesiveness increasing amount of a clay to said adhesive prior to casting.

This invention also relates to a dermal composition. The adhesive dermal composition comprises a mixture of a drug, a pressure sensitive adhesive, a solvent for one or more of the composition components and a minor amount, namely less than about 50% and preferably less than 20% by dry weight of the total composition, of an adhesiveness increasing amount of a clay.

It has been surprisingly found that the addition of a clay to an adhesive, particularly a mixture of a rubber, an ethylene/vinyl acetate and an acrylic polymer pressure sensitive adhesive formulation, results in a pressure sensitive drug composition of desirable peel, adhesion, shear resistance and tack.

The composition can contain other ingredients known for use with transdermal drug delivery compositions. The device is thus a multiphase composition comprising a phase formed of a polymeric matrix having limited water solubility containing in admixture therein a drug. The matrix may be comprised of one or more polymers. The combination of the specific polymers, liquid solvent and solids, such as drug and a clay, available to form an interpenetrating phase in the matrix. When the system is placed on the skin, the drug is released from the matrix at a rapid but decelerating rate.

The clay of this invention can be hydrated aluminum silicate, kaolinite, montmorillonite, atapulgite, illite, bentonite, and halloysite. Preferred clays are those with a three layer structure.

The pressure sensitive adhesive can be any adhesive, which, when combined with a drug, tends to adhere over the conditions of use. A useful adhesive is a mixture of a multipolymer and a rubber, especially a multipolymer containing vinyl acetate and ethylene monomers and acrylic polymer. The rubber can be a natural or synthetic rubber. dr

DETAILED DESCRIPTION OF THE INVENTION INCLUDING PREFERRED EMBODIMENTS

This invention relates to increasing the adhesiveness of a drug-containing pressure sensitive adhesive, namely a dermal composition, by the addition of a clay. The clay is added in an adhesiveness-increasing amount.

This invention also relates to a transdermal drug delivery device or composition comprising a drug, a pressure sensitive adhesive, a liquid solvent for one or more components of the composition and a clay. The clay is present in an adhesiveness-increasing effective amount, namely a minor amount or less than 50% of the total composition, and preferably about 20% or less of the total dry weight of the composition. More preferably the clay constitutes less than 10% or even less than 5% by weight of the total composition. The term "dry weight" as used herein means the weight of the composition after casting and drying This invention also relates to increasing the rate of drug release by the use of a multiphase system comprising a phase formed of a polymer matrix having a limited water solubility and an additional phase or phases comprising one or more of the following a polymer, a liquid such as a solvent and a solid for example a drug or a clay.

The term "clay" as used herein means any natural or synthetic clay and includes hydrated aluminum silicate, kaolinite, montmorillonite, atapulgite, illite, bentonite, and halloysite. Preferred clays are those with a three layer structure.

The term "drug" as used herein means and refers to any substance capable of being administered to the skin of an animal to exert a local or systemic effect. Thus, the term "drug" can include, but is not limited to:

1. Anti-infectives, such as antibiotics, including penicillin, tetracycline, chloramphenicol, sulfacetamide, sulfamethazine, sulfadiazine, sulfamerazine, sulfamethizole and sulfisoxazole; antivirals, including idoxuridine; and other anti-infectives including nitrofurazone and the like;
2. Anti-allergenics such as antazoline, methapyrilene, chlorpheniramine, pyrilamine and prophenpyridamine;
3. Anti-inflammatories such as hydrocortisone, cortisone, dexamethasone, fluocinolone, triamcinolone, medrysone, prednisolone, piroxicam, oxicam and the like;
4. Decongestants such as phenylephrine, naphazoline, and tetrahydrozoline;
5. Miotics and anticholinesterases such as pilocarpine, carbachol, and the like;
6. Mydriatics such as atropine, cyclopentolate, homatropine, scopolamine, tropicamide, ecuatropine and hydroxyamphetamine;
7. Sympathomimetics such as epinephrine;
8. Sedatives, hypnotics, analgesics and anesthetics such as chloral, pentobarbital, phenobarbital, secobarbital, codeine, lidocaine, fentanyl and fentanyl analogs, opiates, opioids, agonists and antagonists therefor;
9. Psychic energizers such as 3-(2-aminopropyl)indole, 3-(2-aminobutyl)indole, and the like;
10. Tranquilizers such as reserpine, chlorpromazine, thiopropazate and benzodiazepines such as alprazolam, triazolam, lorazepam and diazepam;
11. Androgenic steroids such as methyltestosterone and fluoxymesterone;
12. Estrogens such as estrone, 17-beta-estradiol, ethinyl estradiol, and diethylstilbestrol;
13. Progestational agents, such as progesterone, 19-norprogesterone, norethindrone, megestrol, melengestrol, chlormadinone, ethisterone, medroxyprogesterone, norethynodrel 17 alpha-hydroxyprogesterone dydrogesterone, and nomegesterol acetate;
14. Other steroids or steroid like substances such as androgens.
15. Humoral agents such as the prostaglandins, for example $PGE_1$, $PGE_{2alpha}$, and $PGF_{2alpha}$;
16. Antipyretics such as aspirin, salicylamide, and the like;
17. Antispasmodics such as atropine, methantheline, papaverine, and methscopolamine;
18. Anti-malarials such as the 4-aminoquinolines, alpha-aminoquinolines, chloroquine, and pyrimethamine;
19. Antihistamines such as diphenhydramine, dimenhydrinate, perphenazine, and chloropenazine;
20. Cardiovascular agents such as nitroglycerin, isosorbide dinitrate, isosorbide mononitrate, quinidine sulfate, procainamide, flumethiazide, chlorothiazide, calcium antagonists such as nifedipine, verapamil and diltiazem and selective and non-selective beta blockers such as timolol, salbutamol, terbutaline and propranolol, ACE inhibitors such as captopril and various other agents such as clonidine and prazosin.
21. Nutritional agents such as essential amino acids and essential fats.

Other drugs having the same or different physiological activity as those recited above can be employed in drug delivery devices within the scope of the present invention. Although most of the foregoing drugs are solid at room temperature, some drugs are liquid at such temperatures.

Drugs contained in the composition can be in different forms depending on solubility and release characteristics, such as uncharged molecules, components of molecular complexes or pharmacologically acceptable salts or derivatives thereof. Simple derivatives of the drugs such as pharmaceutically acceptable ethers, esters, amides, and the like which have desirable retention and release characteristics but which are easily hydrolyzed at body pH, enzymes, pro-active forms, and the like can be employed.

The amounts of drug for use in the invention are as set forth herein, for example in the accompanying disclosure and examples, and are also known in the art from standard reference books such as Remington's Pharmaceutical Sciences, Seventeenth Edition, Part IV, published by Mack Publishing Co., Easton, Pa. and Goodman and Gilman, "The Pharmacological Basis of Therapeutics", MacMillan Publishing Co., 6th Edition (1980).

The therapeutic dosage and dosage unit amounts for the transdermal route can be determined by standard tests known to those skilled in the art and an estimation of dosage by the in vitro flux data using human cadaver skin. Alternatively, animal skin can be used to estimate dosages as described in U.S. Pat. No. 4,751,087.

The term "pressure sensitive adhesive" as used herein means and refers to polymers, including but not limited to homopolymers, copolymers and mixtures of polymers, which are adhesive in the sense that they can adhere to the skin of an animal and which are pressure sensitive in the sense that adherence can be effected by the application of pressure. The pressure sensitive adhesive can function as a matrix for the drug. The adhesive is sufficiently resistant to chemical and/or physical attack by the environment of use so that it remains substantially intact throughout the period of use. The adhesive is biocompatible in the environment of use, plastically deformable and with limited water solubility solubility. The term "water" as used herein includes water containing biological fluids such as saline and buffers.

A wide variety of polymers are known to be suitable for use in pressure sensitive adhesives. Suitable polymers include a natural or synthetic rubber, acryates, polycarboxylic acids or anhydrides thereof, vinyl acetate polymers and the like. A pressure sensitive adhesive can be composed of a single polymer or mixtures thereof. It is generally found that the preferred polymers for pressure sensitive applications have a glass transition temperature of between about −50 to +10 degrees Celsius (°C.). The glass transition temperature is related to the molecular weight of the adhesive.

A preferred dermal composition of this invention comprises a drug; a multipolymer comprising an ethylene/vinyl acetate polymer and an acrylate polymer; a rubber, a clay and, optionally, a tackifying agent. The multipolymer and rubber are preferably in a ratio by weight respectively from about 1:10 to about 30:1, more desirably about 1:5 to 20:1 and preferably about 1:2 to 15:1. The ratio of ethylene/vinyl acetate polymer to acrylate polymer is preferably about 20:1 to about 1:20 by weight. The clay is present in the composition in an amount by dry weight of less than about 50% and preferably from 0.1 to 20%.

The term "solvent," when used to refer to one or more of the components of the composition, means a substance added to minimize the lack of solubility or dispersibility of one or more of the components in the dermal composition. The solubilities of the components in polar and non-polar solvents of the composition are either known or can easily be determined by known methods.

When a lipophilic drug is used, such as 17-beta estradiol, a fat soluble steroid, the drug has a limited solubility in various polymers used for pressure sensitive adhesives. The addition of a glycol improves the dispersibility of the steroid such as 17-beta estradiol, while maintaining the even distribution of the drug throughout the adhesive. However the addition of glycol and various other liquids to the composition often results in plasticization and thus a reduction in the adhesiveness of the composition.

The use of clay with a liquid drug or a drug in a liquid solvent may minimize any loss of adhesiveness, resulting from the inclusion of the liquid.

This system permits a low loading of medicament and solvent into the dermal composition while maintaining the desirable physical properties and release rate. The system also permits use of a large amount of drugs which plasticize the multipolymer.

The composition of this invention possesses sufficient adhesive properties to remain in place for days with low incidence of debonding. Surprisingly, the clay increases adhesiveness even though it reduces cohesiveness. Generally, changes in cohesiveness are proportional to changes in adhesiveness.

The transdermal drug delivery device of this invention has a defined geometric shape, and has a protective release liner on one side and a backing on the other. The shape is achieved by conventional techniques, e.g. by casting or cutting. Removal of the liner exposes the pressure sensitive adhesive. The pressure sensitive adhesive is backed by a drug impermeable material that may be colored and labeled as appropriate. Suitable release liners and backings are those known in the art for use with pressure sensitive adhesives The composition is especially adapted for use with the delivery of drugs where the weight of the drug is less than 50% of the total weight of the composition, namely where dispersibility is important. The composition is particularly useful where the weight of the drug is less than 10% or even less than 5% of the total weight of the composition.

With the present invention, drugs incorporated into the pressure sensitive adhesive are rapidly released to the skin. The fact that the drug is rapidly released to the skin and may be in a liquid that functions as a solvent, does not in fact negatively affect the rate of permeation through the skin and the resulting blood levels of the drug. Rather, the system permits even delivery of the drug to the blood, particularly a steroidal drug, and with less percent fluctuation of blood levels of drug, namely peak to trough variation, than when controlled diffusion is used. When the device of this invention is placed on the skin, the drug will permeate to and through the skin.

The dermal composition according to the present invention can be prepared, for example, by mixing the adhesive, for example the multipolymer including the acrylate polymer, drug, the rubber, the optional solvent, clay and optional tackifying agent in an appropriate lower molecular weight liquid. Appropriate liquids are preferably volatile polar and non-polar organic liquids, such as an alcohol, such as isopropyl alcohol or ethanol, a benzene derivative such as xylene or toluene, alkanes and cycloalkanes such as hexane, heptane and cyclohexane and an alkanoic acid acetate such as an ethyl acetate. The liquid mixture is cast at ambient pressure and all lower molecular weight liquids removed; for example by evaporation, to form a film The higher boiling solvents such as lower molecular weight alkane diols used in the composition remain therein.

The ethylene/vinyl acetate polymers can be either a copolymer or a terpolymer. Thus a copolymer of vinyl acetate and ethylene can be used. A terpolymer of an acrylic acid/ethylene/vinyl acetate can also be used. Thus the third monomer of the terpolymer can be an acrylic acid such as acrylic acid or methacrylic acid or copolymers thereof The acrylate polymer can be any of the various homopolymers, copolymers, terpolymers and the like of various acrylic acids. The acrylic polymer constitutes preferably from about 5% to about 95% the total weight of the multipolymer, and preferably 25% to 92%, the amount of the acrylate polymer being chosen being dependent on the amount and type of the drug used. Thus the smaller the amount of the drug used, the greater amount of the acrylate polymer can be used.

The acrylate polymers of this invention are polymers of one or more acrylic acids and other copolymerizable functional monomers The acrylate polymer is composed of at least 50% by weight of an acrylate or alkylacrylate, from 0 to 20% of a functional monomer copolymerizable with the acrylate and from 0 to 40% of other monomers Acrylates which can be used include acrylic acid, methacrylic acid and esters thereof, including N-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Funtional monomers copolymerizable with the above alkyl acrylates or methacrylates which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Ethylene/vinyl acetate copolymers and terpolymers are well known, commercially available materials. Typically such polymers have a vinyl acetate content of about 4 percent to 80 percent by weight and an ethylene content of 15 to 90 percent of the total. Preferably the ethylene/vinyl acetate copolymer or terpolymer has a vinyl acetate content of about 4 percent to 50 percent by weight, with a melt index of about 0.5 to 250 grams per ten minutes, and a density having a range of about 0.920 to 0.980. More preferably the polymer has a vinyl acetate content of about 40 percent by weight and a melt index of about 0.5 to 25 grams per ten minutes. Melt index is the number of grams of polymer which can be forced through a standard cylindrical orifice under a standard pressure at a standard temperature and thus is inversely related to molecular weight. As is used in the specification, melt index is determined in accordance with the standard ASTM D 1238-65T condition E.

In addition to varying the percentage of vinyl acetate in the ethylene/vinyl acetate polymer, the properties of the multipolymer can be changed by varying the amount of acrylate.

From the foregoing it can be understood that the multipolymer can be composed of an ethylene/vinyl acetate polymer containing at least about from 15 to 90 percent by weight of ethylene monomer and from about 4 to 80 percent by weight of vinyl acetate monomer, and from about 5 to 95% of an acrylate polymer.

The selection of the particular ethylene/vinyl acetate and acrylate multipolymer, along with the rubber and other agents will be dependent on the particular drug used and the form in which it is added, drug alone or drug plus solvent. By varying the composition, the release rate can be modified, as will be apparent to one skilled in the art.

Selection of the particular multipolymer is governed in large part by the drug to be incorporated in the device, as well as the desired rate of delivery of the drug. Those skilled in the art can readily determine the rate of delivery of drugs from the polymers and select suitable combinations of polymer and drug for particular applications.

The term "rubber" as used herein means a natural or synthetic elastomeric polymer. The rubbers useful in the invention include natural latex (polyisoprene) and carboxylated styrene/butadiene polymers. Other suitable rubbers include styrene copolymers such as styrene-isoprene-styrene block copolymer, polybutylene and polyisobutylene, synthetic polyisoprene, butyl rubber and silicone rubber.

To the extent the tackifying agent is a natural or synthetic rubber, references herein to amounts of a rubber in the composition includes the rubber used as a tackifier.

The rubber elastomers are used to promote the adhesiveness of the composition particularly suitable elastomers include the synthetic rubbers, particularly those having a molecular weight distribution approximating that of natural rubber latex or natural rubber latex itself.

The ratio by weight of multipolymer to rubber is preferably about 1:10 to about 30:1 respectively and more preferably about 1:5 to about 20:1, and even more preferably 1:2 to 15:1, the amount of rubber used being selected to preferably achieve a tack of 200 to 800 grams per square centimeter and more preferably 300 to 500 grams per square centimeter (ASTM D 2979) and adhesion of about 1 to 3 pounds per linear inch (ASTM D 903-49).

In general, the composition should have a glass transition temperature (Tg), measured using a differential scanning calorimeter, of between about $-70°$ C. to $0°$ C. and be a pressure sensitive adhesive at room temperature.

The expression "limited water solubility" of the pressure sensitive adhesive as used herein denotes the ability of the adhesive to function in the device of this invention. The phrase means that the polymer has a limited ability to be dissolved in or absorb water and like highly polar liquids. This hydrophobicity is important in the sense that the adhesive be of limited solubility in water and like biological fluids over prolonged periods of time. One procedure for determining water absorption of a given polymer comprises immersing a dry, measured section of the polymer in water at $20°$ C. for 24 hours. After removal of the polymer from the water it is reweighed and the weight gain is expressed as a percent by weight of the polymer, of the water absorbed. Detailed procedures are known to persons skilled in the art.

The transdermal drug delivery device can additionally contain additives suitable for use with transdermal drug delivery devices such as tackifiers, softeners, penetration enhancers and various other ingredients used in transdermal formulations.

The device can also include a filler. Fillers have been used in the adhesive industry to reduce the cost of polymers, increase the specific gravity and to raise the viscosity of adhesive formulations. Various ingredients have been used as fillers including allantoin, zinc oxide, calcium carbonate, sorbitol, silicas, cellueose derivates such as methylcellulose, carboxymethylcellulose and polyvinyl alcohol. The addition of these hydrophilic fillers, emulsifiers and suspending agents has not been found to improve adhesiveness, as does the addition of clay.

The amount of drug to be incorporated in the composition varies depending on the particular drug, the desired therapeutic effect and the time span for which the device provides therapy. For most drugs, the passage through the skin will be the rate limiting step. Thus, the amount of drug and the rate of release is typically selected so as to provide delivery characterized by substantially zero order time dependency for a prolonged period of time. The minimum amount of drug in the system is selected to deliver the drug at least at the rate at which the drug passes through the skin in the time span for which the device is to provide therapy. Conveniently, the amount of drug in the system can vary from about 0.1 to about 50% by weight. As dosages increase to more than 50% by weight, wear is seriously affected and generally a larger unit would be used in lieu of an increased amount of drug.

Clays belong to two groups In the kaolinite group, the mineral is characterized by a two-layer (1:1) lattice consisting of one octahedral layer linked to one silica tetrahedral layer. This lattice does not expand with varying water content and no replacement of iron or magnesium in the octahedral layer are known. The other group of clay minerals is characterized by a three-layer (2:1) lattice. In this type of lattice an alumina octahedral layer is sandwiched between two silica tetrahedral layers.

Figure 1:
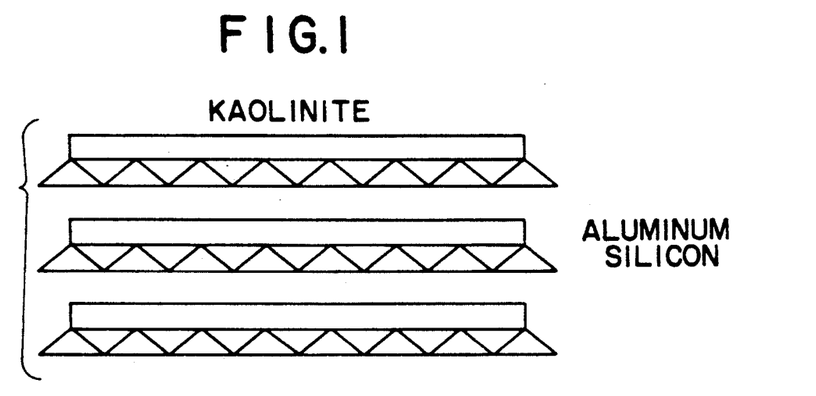
FIG. 1 illustrates the structure of the kaolinite.
Figure 2:
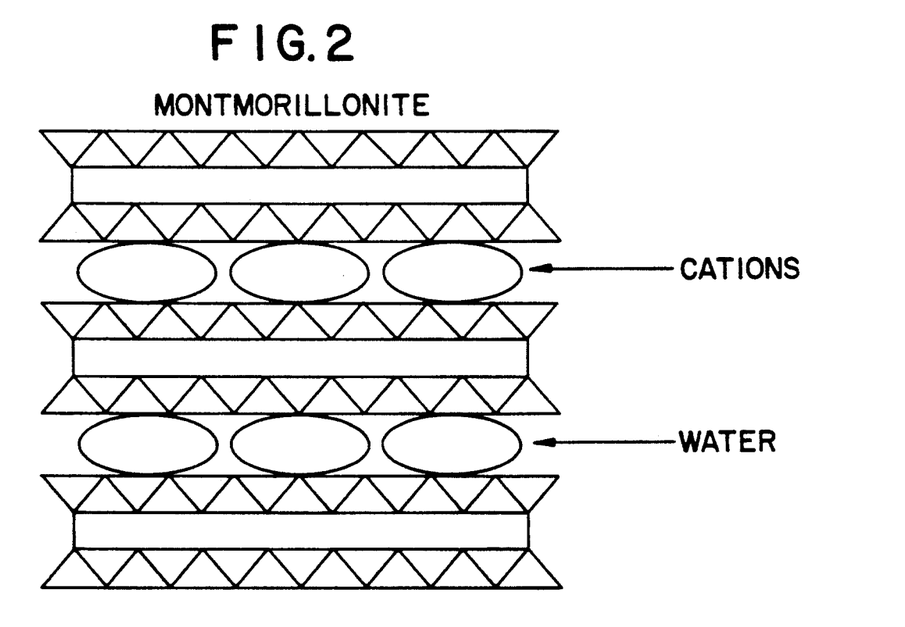
FIG. 2 illustrates the structure of montmorillonite.
Figure 3:
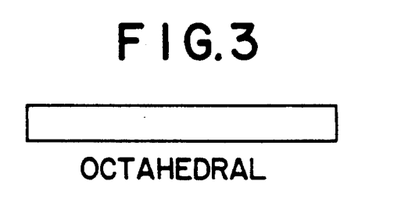
FIG. 3 illustrates the structure of the octahedral layer of a clay.
Figure 4:
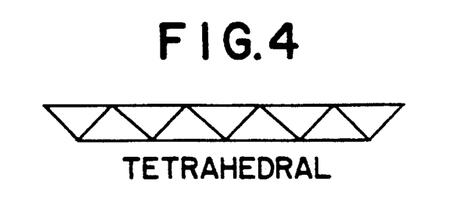
FIG. 4 illustrates the structure of the tetrahedral layer of a clay.

As seen in FIG. 1, kaolinite has a two-dimensional structure. As seen in FIG. 2 montmorillonite has a three-dimensional structure, a preferred structure.

Bentonite, known as purified bentonite, is colloidal montmorillonite processed to remove grit and non-swellable ore components.

Montmorillonite is one of several important clays belonging to the three-layer group In montmorillonite these three-layer units are loosely held together in the c-direction, namely the cross-section or axis perpendicular to the layers, with water and cations between them. Montmorillonite is the principal clay mineral of bentonite. Some of the outstanding features of montmorillonite are the expandability of the crystal lattice and the presence of cations between the unit layers. The amount of water between the layers varies so that the total c-dimension ranges from 9.6 to 21.4 angstrom units. In water, the cations between the unit layers can be exchanged by cations available in solution Montmorillonite is also capable of forming organic-montmorillonite complexes with certain organic molecules.

The amount of clay to be added to the formulation is an adhesiveness increasing amount of clay up to a maximum amount. The maximum amount is that which reduces the cohesive strength of the transdermal drug delivery device resulting in reduced rate of drug delivery or reduced wear time or both. Reduced wear time is lower than required for the dosage form, usually less than 12 hours. In practice although amounts of clay from about 0.1% to 20% or even up to 50% based on the total weight of the composition may be used, preferred amounts are about 1 to 6%, especially where lower drug and solvent levels are used. Higher amounts of clay results in loss of cohesive strength.

Surprisingly, it has been found that for 17-beta-estradiol, use of the Present composition (as set forth in Example 1 below) results in not only an exponential release to the skin, but lowered percent fluctuation of blood level over time.

In order to determine the adhesiveness increasing amount, wear tests are performed using adhesive-coated strips of the adhesive to be tested on ten or more selected individuals. The strips may or may not contain the drug. In the wear tests, a strip of adhesive is adhered to an individual in the proposed area of use for the prescribed period of time. The amount of time the strip sticks to the individual is recorded. A strip is considered to be sufficiently adhesive if its duration of adhesion in most of the individuals is the intended wear time, which can vary from 12 hours to one week or more.

The actual percentages of clay for any given polymer system can be determined by subjecting various transdermal drug delivery devices containing varying amounts of clay to the test previously indicated in the previous paragraph. The amount of clay is related to the type and percent by weight of drug and liquids in the system. The actual amount of clay used is typically less than the weight of the liquid.

By adjusting the type and amount of multipolymer, rubber, drug, tackifying agent and clay, it is possible to produce a composition that can be effectively utilized as a transdermal drug delivery system. The interacting effects of the drug, multipolymer, rubber and tackifying agent make it possible to improve the stability, adhesion, wear and amount of drug delivery per unit area. The desirable composition is non-irritating to the skin. Further, the composition should be sufficiently adhesive so as to firmly adhere to the skin, even when subjected to adverse conditions such as humidity, perspiration, movement, showers and/or bathing, but not so adhesive as to cause irritation to the skin or substantial discomfort to the patient when removed from the skin. Further, all components used must be compatible with the drug.

The composition can also contain agents known to accelerate the release of the drug onto the body surface or through the skin. This class of agents includes those with diverse mechanisms of action including those which have the function of improving the release rate of the drug from the multipolymer and those which improve percutaneous absorption. For example, absorption, can be accelerated by changing the *stratum corneum's* (skin) ability to retain moisture, softening the skin, improving the skin's permeability, acting as penetration assistants or hair-follicle openers or changing the state of the skin including the boundary layer. Some of these agents have more than one mechanism of action. Some examples of these enhancers are glycols such as diethylene glycol, dipropylene glycol, butylene glycol, propylene glycol or polyethylene glycol which may enhance drug solubility, oils such as olive oil, squalene or lanolin, fatty acid ethers such as cetyl ether and oleyl ether and fatty acid esters such as myristyl proprionate which enhance drug diffusibility, urea and urea derivatives such as allantoin which affect the ability of keratin to retain moisture, polar solvents such as dimethyldecylphosphoxide, methyloctyl-sulfoxide, dimethyllaurylamide, dodecylpyrrolidone, iso-sorbitol, dimethylacetonide, dimethylsulfoxide, decylmethylsulfoxide and dimethylformamide which affect keratin permeability, salicylic acid which softens the keratin, amino acids which are penetration assistants, benzyl nicotinate which is a hair follicle opener, and higher molecular weight aliphatic surfactants such as lauryl sulfate salts which change the surface state of the skin and drugs administered. Other agents include linoleic and ascorbic acids, panthenol, butylated hydroxytoluene, propyl oleate and propyl or isopropyl myristates.

Some drugs, such as the vasodilator nitroglycerin, function as a plasticizer because they are soluble to a certain degree in the polymer. For drug molecules which are not readily soluble in the polymer, a solvent for the drug and polymer can be added. Such solvents, such as, lecithin, retinol derivatives, tocopherol, dipropylene glycol, triacetin, propylene glycol, saturated and unsaturated fatty acids, mineral oil, alcohols, butyl benzyl pthalate, and the like are useful solvents depending on the solubility of the drug chosen. These solvents are of a volatility that they do not substantially evaporate on drying of the cast device.

The adhesive layer of the device of this invention is backed by a material which prevents the escape of the active ingredient. This backing layer is desirably selectively permeable, for example to oxygen, with a suitable water vapor transmission rate so that the transdermal drug delivery system will "breathe," allowing the skin to maintain a more natural state. The permeable backing should not permit passage of the drug. However the backing layer may be a relatively non-permeable material, such as, metal foil (example: aluminum), polyolefin (example: polyethylene or polypropylene), polyester (example: polyethylene terephthalate), and polyamide.

The device of this invention has an interpenetrating phase comprising an agglomerate or clusters of one or more of polymer, drug, solvent or clay that form a network of substantially contiguous zones in the pressure sensitive adhesive. The network can be a lightly to highly branched plurality of clusters or it can be a short to long linear chain plurality of clusters.

The rate of release of the drug from the device of this invention can be easily determined by those skilled in the art by using standard procedures. In this manner, particular materials used as the pressure sensitive adhesive, as well as the drug, solvent and clay, can be designed and programmed for an intended result.

Preferred and optimum compositions are as follows:

TABLE

| Component | PERCENT BY WEIGHT (dry) | | |
|---|---|---|---|
| | Optimum Amount | Preferred Range | Suitable Range |
| Rubber | 5 | 2 to 20 | 0–90 |
| Acrylate | 55 | 25 to 70 | 0–90 |
| Ethylene-Vinyl Acetate | 5 | 3 to 20 | 0–90 |
| Polyisobutylene | 13 | 3 to 20 | 0–40 |
| Lecithin | 3 | 1 to 10 | 0–30 |
| Propylene Glycol | 1 | 0.5 to 10 | 0–20 |
| Butylene Glycol | 2 | 0.5 to 10 | 0–20 |
| Dipropylene Glycol | 1 | 0.5 to 10 | 0–20 |
| Oleic Acid | 7 | 0.2 to 10 | 0–20 |
| Clay | 3 | 0.1 to 6 | 0.2–20 to 50 |
| Mineral Oil | 2 | 0.5 to 4 | |
| Drug | 3 | 0.5 to 6 | 0.5–50 |
| | 100.0% | | |

EXAMPLES

In the following examples, "Airflex" refers to a trademark of Air Products and Chemicals Inc., Allentown, Pa. for a group of optionally carboxylated vinyl acetate/ethylene polymers in aqueous emulsion. "Airflex 416" is a carboxylated vinyl acetate/ethylene terpolymer and has the following properties:

| Solids | 52% min. |
|---|---|
| Viscosity (cps) | 1500–2500 |
| pH | 3.5 to 5 |
| Density | 8.8 lbs. per gal. |

The same type of polymer, "Airflex 426" has the properties:

| | |
|---|---|
| Viscosity (20 rpm) (cps) | 1,000–1,500 |
| pH | 4.5–5.0 |
| Tg (°C.) | −5 to 0 |
| Intrinsic Viscosity In Toluene | 0.3–0.4 |
| Swell Index | 17.5–22.5 |

"Airflex 400", "Airflex 405" and "Airflex 465 DEV" are trademarks of Air Products and Chemicals Inc., Allentown, Pa. for a group of vinyl acetate/ethylene copolymers supplied as aqueous emulsions.

"ADCOTE 72A103" also called "Morstik 103" is a trademark of Morton Thiokol, Chicago, Ill. for a styrene butadiene styrene ("S-B-S") block copolymer rubber.

"ALCOLEC" is a trademark of American Lecithin Company Atlanta, Georgia for lecithin sold as ALCOLEC 6622 PG 60% by weight in propylene glycol.

"AEROTEX 3730" resin is a trademark of American Cyanamid, Wayne, N.Y. for a melamine formaldehyde crosslinking agent for various functional groups, including carboxyl groups having a density of 10.5 lbs. per gallon.

"AIRFLEX 400" has the following properties:

| | |
|---|---|
| Viscosity | 1900–2800 cps @ 20 rpm (77° F.) |
| Tg | 0° C. |
| pH | 4.0 to 5.0 |
| density | 8.9 lb per gal. |

"AIRFLEX 405" has the following properties:

| | |
|---|---|
| Viscosity | 300–1000 cps @ 20 rpm (25° C.) |
| Tg | 7° C. |
| pH | 5.0 to 6.0 |
| density | 9.0 lb per gal. |

"AIRFLEX 465 DEV" has the following properties:

| | |
|---|---|
| Viscosity | 800–1300 cps @ 20 rpm (77° F.) |
| Tg | −5° C. |
| pH | 4.5 to 5.5 |
| density | 9.0 lb per gal. |

"DURO-TAK 36-6172" is a trademark of National Starch and Chemical Corporation, Bridgewater, N.J. for a solution of a resin modified styrene butadiene block copolymer with terpene resins and rosin ester resins having softening points of 100° C.

"DURO-TAK 80-1194 and 80-1196 and 80-1054" are trademarks of National Starch for polyacrylates in organic solution. "DURO-TAK 80-1194 and 80-1196" consist of methacrylic acid, 0–3%, butylacrylate, 2-ethylhexylacrylate and other monomers, such as vinyl acetate.

"ELVAX 40-W" is a trademark of Dupont for an ethylene/vinyl acetate polymer which has the following typical properties:

| | |
|---|---|
| Vinyl Acetate (VAc) Content, % by weight | 40 |
| Inherent Viscosity @ 30° C. (0.25 g/100 ml. toluene) | 0.70 |
| Melt Index, g/10 min. (ASTM D 1238, modified) | 57 |
| Residual VAc Monomer, % by wt. | less than about 0.3 |
| Odor | Slight |
| Antioxidant, ppm BHT | 550 |
| Tensile Strength[a], MPa (psi) | 4.8–6.2 (750–900) |
| Elongation at Break[a], % | 1000–1300 |
| Elastic (Tensile) Modulus[a,b], MPa (psi) | 3.0 (450) |
| Density @ 23° C. (73° F.), kg/m³ (ASTM D 1505) (G/cm³) | 965 (0.965) |
| Hardness, Shore A-2 Durometer, 10 sec (ASTM D 2240) | 40 |
| Softening Point, Ring and Ball, °C. (ASTM E 28) (°F.) | 104 (220) |

[a]ASTM D 1708; samples die cut from pressed films; gage dimensions 2.23 cm × 0.47 cm × 0.13 cm (0.876 in × 0.187 in × 0.050 in); crosshead speed 5.1 cm (2 in)/min.
[b]Modulus calculated as in ASTM D 638.

"ESCOREZ RESIN 1310LC and 2101 and 2393" are a trademark of Exxon Chemical Company, Baton Rouge, La. for aliphatic (1310LC) and aliphatic/aromatic (2101 & 2393) resins functioning as a tackifier.

"EXXON 108A" emulsion is the trademark of Exxon Chemical Company, Baton Rouge, La. for an aliphatic petroleum resin tackifying agent having a glass transition temperature of 40° C., a pH of 7.0 and an average particle size of 0.33 microns, and an anionic particle charge.

"EXXON 109A" emulsion is the trademark of Exxon Chemical Company, Baton Rouge, La. for a mixed aromatic/aliphatic petroleum resin tackifying agent in an aqueous emulsion having a glass transition temperature (Tg) at 37° C., a pH of 7.0, with an average particle size of 0.5 microns and an anionic particle charge.

"EXXON 346" is a trademark of Exxon Chemical Company for a mixed aromatic/aliphatic petroleum resin tackifying agent having a Tg of 25° C., a pH of 7.0, an average particle size of 0.35 microns and an anionic particle charge.

"FLEXBOND 150" is a trademark of Air Products and Chemicals, Inc., Allentown, Pa. for a polyvinylacetate polymer which is a pressure sensitive emulsion which can function as a tackifying agent.

"HARTEX 103" is a trademark of Firestone Synthetic Rubber and Latex Company for low-ammonia natural latex (rubber) containing 0.036% sodium dimethyldithiocarbamate and 0.036% zinc oxide as a preservative. The properties of this latex are as follows:

| | |
|---|---|
| Total Solids | 62.1 ± 0.3 61.5 min. |
| Dry Rubber Content, % | 60.0 min. |
| TS minus DRC, % | 1.75 max. |
| Total Alkalinity, % NH on wet weight | .24 ± .02 |
| KOH Number | 0.55 ± 0.05 |
| Mechanical Stability, sec. | 1400 ± 300 |
| Volatile Fatty Acid, % | .05 max. |
| pH | .8 ± 0.20 |
| Sludge Content, % on weight | .03 max. |

"HATCOL 200" is a trademark of Hatco Chemical Company, Fords, N.J., for a high molecular weight synthetic ester plasticizer having a molecular weight of 546 and a viscosity @20° C. of 300 CPS.

"KORTHIX H-NF" is a trademark of Kaopolite, Inc., Union, N.J. for bentonite, a purified colloidal aluminum silicate (clay).

"NOVEN 109A" is a trademark of Noven Pharmaceuticals, Inc., Miami, Fla., for the combination of 140 parts of the anhydrous resin Exxon 109A, 70 parts toluene and 7 parts Triton X-100. TRITON X-100 is a trademark of Rohm and Haas Company for the water soluble, anhydrous, nonionic surfactant octylphenoxypolyethoxyethanol with an average of 10 moles of ethylene oxide, having a viscosity of 240 cps @25° C. (Brookfield), a pour point of 7° C. or 45° F., a specific gravity of 1.065 @25° C. and a density of 8.9 lb. per gallon.

"PSA 578A" is the trademark of Dow Chemical, Midland, Minn. for carboxylated styrene/butadiene containing a bactericide and a stabilizer. The formulation has a boiling point of 100° C., a vapor pressure of 17.5 millimeters of mercury at 20° C., a Tg. at −44° C. a vapor density of 0.624 at 80° F., is supplied in emulsion form with a milky white liquid appearance and has a specific gravity of 0.980-1.040.

"Santicizer 160" is a trademark of Monsanto, St. Louis, Mo. for butyl benzyl phthalate.

"VISTANEX LM-MS-LC" is trademark of Exxon Chemical Company, Houston, Tex. for a polyisobutylene having a flory molecular weight of 37,000 minimum by AMS Test Method 77-005, a specific gravity of 0.91 and a Brookfield Viscosity, CPS @350° F., of 26,000 to 35,000 by ASTM Text Method 03236.

Nitroglycerin can be supplied as glyceryltrinitrate available in an ethanol solution from Imperial Chemical Industries.

All the polymeric ingredients used in the examples are supplied or used as aqueous emulsions or as solutions wherein the percent solids are as follows:

| Ingredient | Percent Solids (by weight) |
|---|---|
| Airflex 400 | 55% |
| Airflex 405 | 55 |
| Airflex 416 | 52 |
| Airflex 426 | 60 |
| Airflex 465 | 66 |
| Hartex 103 | 61.5 |
| PSA 578A | 49 |
| Exxon 108A | 57 |
| Exxon 109A | 57 |
| Exxon 346 | 57 |
| Elvax 40W | 30 |
| Noven 109A | 35 |
| Flexbond 150 | 55 |
| Aerotex 3730 | 83 |
| Duro-Tak 36-6172 | 56 |
| Duro-Tak 80-1194 | 45 |
| Duro-Tak 80-1054 | 48 |
| Duro-Tak 80-1196 | 45 |
| Adcote 72A103 (Morstik 103) | 45 |
| Vistanex | 30 |

The general method of preparation of the adhesive is per the following steps:

1. Appropriate amounts of adhesive, e.g. rubber, tackifying agent and adhesive multipolymer are combined, and thoroughly mixed together in a vessel; since pressure sensitive adhesive formulations are typically supplied as emulsions or solutions, the preparation of the composition is typically performed in liquid solution or suspension, but can as well be formed by methods not requiring the presence of a liquid as discussed herein.
2. The heterogeneous mixture is then transferred to a vessel where the drug or drug and cosolvent and clay are to be added;
3. The drug, solvent, and clay are then added to the heterogenous mixture and agitation is carried out until the mixture and drug form a smooth, heterogeneous mix;
4. The heterogeneous mix containing the drug is then transferred to an adhesive mixing vessel;
5. The mix containing the drug can then be combined with a crosslinking agent and any additional optional ingredients and thoroughly agitated;
6. The adhesive containing the drug is then transferred to a coating operation;
7. The adhesive composition containing the drug is now in a form to make up the adhesive layer to be coated onto a release liner. When the adhesive composition has been coated onto the release liner, the unit is then passed into an oven in order to drive off the solvents and/or water which may have been included in the mixing procedure; and after this operation is completed and the solvents are removed, the adhesive-component layer will be joined to the backing material and the unit can be wound into rolls for storage.

The order of steps, the amount of the ingredients, pH, and the amount and time of agitation or mixing may be important to avoiding clumping together of the components. These factors can be adjusted by those skilled in the art, while keeping in mind the object of providing a smooth, heterogeneous mix.

A number of other methods, including changing some of the order of steps, can be carried out and will give desirable results.

In addition to having various shapes, the dosage units produced may come in various sizes. A surface area in the range of 1 to 200 square centimeters is contemplated and the presently contemplated, preferred sizes are: 5, 10, 15, 20, 30, 40 and 60 square centimeters. The present invention allows incorporation of the amount of drug that is sufficient to deliver the required dose, no greater than the amount that would yield undesirable properties.

The present invention is further illustrated by the following examples, which should not be considered to limit the invention.

In the following examples parts are given as parts by weight, of the final composition, dry weight.

EXAMPLE 1

30% Ethylene Vinyl Acetate Mixture

Twenty eight parts of toluene is weighed and dispensed into a clean stainless steel kettle. Agitation is started at 44 revolutions per minute ("RPM"). Heating is started with temperature controlled between 120° and 125° F. Twelve parts of ethylene vinyl acetate copolymer (Elvax 40W) is weighed and added to the kettle through the upper hatch while mixing and heating continues. The material is mixed for a minimum of two hours from the time aforementioned temperature is reached. The mixture is transferred to clean containers which are tightly sealed.

30% Polyisobutylene Mixture

Twenty-eight parts of toluene are weighed and dispensed into a clean stainless steel kettle. Agitation is started at 44 RPM's. Heating is started with temperature control set between 145° and 150° F. Twelve parts of polyisobutylene are weighed and added to the kettle while mixing and heating continues. The material is mixed for a minimum of two hours from the time aforementioned temperature is reached. The mixture is transferred to clean containers.

Bulk Adhesive

The following ingredients are mixed: 732 parts of the 30% ethylene vinyl acetate mixture prepared as above, 1899 parts of the 30% polyisobutylene mixture prepared as above, 487 parts of S-B-S block copolymer (Adcote 72A103; Morstik 103), 307 parts of oleic acid NF, 88 parts of mineral oil USP and 250 parts of 60% lecithin in propylene glycol (Alolec 662/PG).

The above ingredients are agitated for a minimum of 10 minutes at 44 RPM. To the foregoing mixture, 5223 parts of acrylic polymer (Duro Tak 80-1196) is added. Heating is started with temperature set between 120 and 125° F and the material is agitated for a minimum of 30 minutes, then 145 parts of clay, namely bentonite N.F. are added portionwise to ensure complete mixing. To the resulting mixture is added an intimate mixture of 702 parts of 1,3-butylene glycol, 44 parts of dipropylene glycol and 123 parts of micronized 17-beta-estradiol USP.

Coating

A specified amount of the bulk adhesive is coated on a silicone coated release liner and most of the low boiling solvents associated with the bulk processing removed, and the dried adhesive is laminated to a backing.

The resulting composition has the following ingredients in the indicated amount.

| COMPONENT | PERCENT BY WEIGHT (dry) |
| --- | --- |
| 1. Rubber (ADCOTE 72A103) | 5.0 |
| 2. Acrylic (Duro-Tak 80-1196) | 53.7 |
| 3. Ethylene Vinyl Acetate (ELVAX 40W) | 5.0 |
| 4. Polyisobutylene (Vistanex LM-MS-LC) | 13.0 |
| 5. Oleic Acid | 7.0 |
| 6. Lecithin | 3.4 |
| 7. Propylene Glycol | 0.4 |
| 8. Dipropylene Glycol | 0.5 |
| 9. Butylene Glycol | 4.0 |
| 10. Clay (Korthix H-NF) | 3.3 |
| 11. Mineral Oil | 2.0 |
| 12. 17-beta-Estradiol | 2.7 |
|  | 100.0 |

Slitting

In order to yield the maximum utilization of the rolls of laminate, they are slit to a specified width according to the size of the patch to be punched.

Punch, Pouch, and Packaging

The role is cut to the desired shape by use of an appropriate shaped die and the resulting device packaged.

In the following examples, the method of Example 1 is used with the appropriate starting material to yield compositions having the following compositions:

| COMPONENT | PERCENT BY WEIGHT (dry) |
| --- | --- |
| EXAMPLE 2 | |
| 1. Rubber (ADCOTE 72A103) | 5.0 |
| 2. Acrylic (Duro-Tak 80-1194) | 51.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 7.5 |
| 7. Butylene Glycol | 7.0 |
| 9. Clay (Korthix H-NF) | 3.0 |
| 10. 17-beta-Estradiol | 2.5 |
|  | 100.0 |
| EXAMPLE 3 | |
| 1. Rubber (ADCOTE 72A103) | 5.0 |
| 2. Acrylic (Duro-Tak 80-1194) | 53.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 4.5 |
| 7. Propylene Glycol | 3.0 |
| 8. Butylene Glycol | 3.0 |
| 9. Dipropylene Glycol | 2.0 |
| 10. Clay (Korthix H-NF) | 3.0 |
| 11. 17-beta-Estradiol | 2.5 |
|  | 100.0 |
| EXAMPLE 4 | |
| 1. Rubber (ADCOTE 72A103) | 5.0 |
| 2. Acrylic (Duro-Tak 80-1194) | 52.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 4.5 |
| 7. Propylene Glycol | 3.0 |
| 8. Dipropylene Glycol | 6.0 |
| 9. Clay (Korthix H-NF) | 3.0 |
| 10. 17-beta-Estradiol | 2.5 |
|  | 100.0 |
| EXAMPLE 5 | |
| 1. Rubber (ADCOTE 72A103) | 5.0 |
| 2. Acrylic (Duro-Tak 80-1194) | 52.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 4.5 |
| 7. Propylene Glycol | 3.0 |
| 8. Butylene Glycol | 5.0 |
| 9. Dipropylene Glycol | 1.0 |
| 10. Clay (Korthix H-NF) | 3.0 |
| 11. 17-beta-Estradiol | 2.5 |
|  | 100.0 |
| EXAMPLE 6 | |
| 1. Rubber (ADCOTE 72A103) | 5.0 |
| 2. Acrylic (Duro-Tak 80-1194) | 47.0 |
| 3. Ethylene Vinyl Acetate (ELVAX 40W) | 5.0 |
| 4. Polyisobutylene-Vistanex LM-MS-LC | 12.0 |
| 5. Oleic Acid | 7.0 |
| 6. Lecithin | 4.5 |
| 7. Propylene Glycol | 10.0 |
| 8. Butylene Glycol | 3.0 |
| 9. Clay (Korthix H-NF) | 3.0 |
| 10. Mineral Oil | 1.0 |
| 11. 17-beta-Estradiol | 2.5 |
|  | 100.0 |
| EXAMPLE 7 | |
| 1. Rubber (ADCOTE 72A103) | 5.0 |
| 2. Acrylic (Duro-Tak 80-1194) | 49.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 4.5 |
| 7. Propylene Glycol | 8.0 |
| 8. Butylene Glycol | 3.0 |
| 9. Clay (Korthix H-NF) | 3.0 |
| 10. Mineral Oil | 1.0 |
| 11. 17-beta-Estradiol | 2.5 |
|  | 100.0 |
| EXAMPLE 8 | |
| 1. Rubber (ADCOTE 72A103) | 5.0 |

-continued

| COMPONENT | PERCENT BY WEIGHT (dry) |
|---|---|
| 2. Acrylic (Duro-Tak 80-1194) | 51.0 |
| 3. Ethylene vinyl Acetate (ELVAX 40W) | 5.0 |
| 4. Polyisobutylene (Vistanex LM-MS-LC) | 12.0 |
| 5. Lecithin | 4.5 |
| 6. Propylene Glycol | 6.0 |
| 7. Butylene Glycol | 3.0 |
| 8. Oleic Acid | 6.0 |
| 9. Clay (Korthix H-NF) | 3.0 |
| 10. Mineral Oil | 2.0 |
| 11. 17-beta-Estradiol | 2.5 |
| | 100.0 |

EXAMPLE 9

| COMPONENT | PERCENT BY WEIGHT (dry) |
|---|---|
| 1. Rubber (ADCOTE 72A103) | 5.0 |
| 2. Acrylic (Duro-Tak 80-1194) | 51.0 |
| 3. Ethylene Vinyl Acetate (ELVAX 40W) | 5.0 |
| 4. Polyisobutylene (Vistanex LM-MS-LC) | 12.0 |
| 5. Lecithin | 4.5 |
| 6. Propylene Glycol | 7.0 |
| 7. Butylene Glycol | 3.0 |
| 8. Oleic Acid | 6.0 |
| 9. Clay (Korthix H-NF) | 3.0 |
| 10. Mineral Oil | 1.0 |
| 11. 17-beta-Estradiol | 2.5 |
| | 100.0 |

EXAMPLE 10

| COMPONENT | PERCENT BY WEIGHT (dry) |
|---|---|
| 1. Rubber (ADCOTE 72A103) | 5.0 |
| 2. Acrylic (Duro-Tak 80-1194) | 50.5 |
| 3. Ethylene Vinyl Acetate (ELVAX 40W) | 5.0 |
| 4. Polyisobutylene (Vistanex LM-MS-LC) | 12.0 |
| 5. Oleic Acid | 7.5 |
| 6. Lecithin | 4.5 |
| 7. Propylene Glycol | 7.0 |
| 8. Butylene Glycol | 3.0 |
| 9. Clay (Korthix H-NF) | 3.0 |
| 10. 17-beta-Estradiol | 2.5 |
| | 100.0 |

EXAMPLE 11

| COMPONENT | PERCENT BY WEIGHT (dry) |
|---|---|
| 1. Rubber (ADCOTE 72A103) | 5.0 |
| 2. Acrylic (Duro-Tak 80-1194) | 53.0 |
| 3. Ethylene Vinyl Acetate (ELVAX 40W) | 5.0 |
| 4. Polyisobutylene (Vistanex LM-MS-LC) | 12.0 |
| 5. Oleic Acid | 5.0 |
| 6. Lecithin | 4.5 |
| 7. Propylene Glycol | 7.0 |
| 8. Butylene Glycol | 3.0 |
| 9. Clay (Korthix H-NF) | 3.0 |
| 10. 17-beta-Estradiol | 2.5 |
| | 100.0 |

EXAMPLE 12

| COMPONENT | PERCENT BY WEIGHT (dry) |
|---|---|
| 1. Rubber (ADCOTE 72A103) | 5.0 |
| 2. Acrylic (Duro-Tak 80-1196) | 47.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 4.5 |
| 7. Propylene Glycol | 4.0 |
| 8. Dipropylene Glycol | 5.0 |
| 9. Butylene Glycol | 3.0 |
| 10. Clay (Korthix H-NF) | 3.0 |
| 11. Mineral Oil | 2.0 |
| 12. 17-beta-Estradiol | 2.5 |
| | 100.0 |

EXAMPLE 13

| COMPONENT | PERCENT BY WEIGHT (dry) |
|---|---|
| 1. Rubber (ADCOTE 72A103) | 5.0 |
| 2. Acrylic (Duro-Tak 80-1196) | 51.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 4.5 |
| 7. Propylene Glycol | 5.0 |
| 8. Dipropylene Glycol | 6.0 |
| 9. Clay (Korthix H-NF) | 3.0 |
| 10. Mineral Oil | 1.0 |
| 11. 17-beta-Estradiol | 2.5 |
| | 100.0 |

EXAMPLE 14

| COMPONENT | PERCENT BY WEIGHT (dry) |
|---|---|
| 1. Rubber (ADCOTE 72A103) | 5.0 |
| 2. Acrylic (Duro-Tak 80-1196) | 48.0 |
| 3. Ethylene Vinyl Acetate (ELVAX 40W) | 5.0 |
| 4. Polyisobutylene (Vistanex LM-MS-LC) | 12.0 |
| 5. Oleic Acid | 7.0 |
| 6. Lecithin | 4.5 |
| 7. Propylene Glycol | 5.0 |
| 8. Dipropylene Glycol | 6.0 |
| 9. Clay (Korthix H-NF) | 3.0 |
| 10. Mineral Oil | 2.0 |
| 11. 17-beta-Estradiol | 2.5 |
| | 100.0 |

The dosage unit of the present invention can be produced in a number of ways. It is particularly important to form the adhesive layer in a series of steps, with proper agitation and pH adjustment when necessary, so as to avoid coagulation and clumping together of any of the components. After the adhesive layer is formed, the composition making up this layer can be placed in contact with the backing layer in any manner known to those skilled in the art in order to produce the transdermal dosage system. The transdermal dosage system can be produced as follows:

Generally speaking, known methods of producing adhesive tapes can be used for the composition of this invention. These known methods including calender coating method, hot melt coating method, solution coating method, emulsion coating method and radiation cured coating method. When dealing with explosive or easily degraded drugs such as nitroglycerin, the solution or emulsion coating method is preferred to minimize the risk of explosion or degradation.

In the calender coating method, the multipolymer, rubber, tackifier and other ingredients are kneaded homogeneously using open rolls, kneaders, internal mixers, etc. The materials of high viscosity have to be kneaded at elevated temperatures, usually 90° to 120° C. under high shear rate ($1 \times 10$ to $5 \times 10^3$ sec.$^{-1}$). In the hot melt coating method the substances with high thermal plasticity are added to the adhesives and the adhesives are coated at high velocity. In the emulsion coating method, the emulsion of the ingredients is added to the appropriate coating head and the excess solvent removed. The solution coating method is essentially the same as the emulsion coating method, except that the mixture is in solution rather than in an emulsion.

The backing member for the adhesive includes plastic films of polyethylene, vinyl acetate resins, ethylene/vinyl alcohol, ethylene/vinyl acetate copolymers, polyvinyl chloride, polyurethane, and the like, metal foils, for example aluminum foil, and the like, non-woven fabric, cloth and laminate films composed of cloth or paper and a basic film. The backing material preferably has a thickness of from 2 to 1,000 micrometers so as to have good handling properties and "feel". A total thickness of the film-like adhesive material on the backing member preferably ranges from 12 to 250 micrometers. Composite products having a total thickness less than 14 micrometers may have poor handling properties.

What is claimed is:

1. A method of increasing the adhesiveness of a pressure sensitive adhesive composition comprising an admixture of a natural or synthetic rubber and a multipolymer comprising a ethylene/vinyl acetate polymer and an acrylic polymer, in which the ratio by weight of the ethylene/vinyl acetate polymer to the acrylic polymer is about 1:20 to about 20:1 and the ratio by weight of the multipolymer to the rubber is about 1:10 to about 30:1.

said method comprising the step of admixing said rubber, said acrylic polymer, said ethylene/vinyl acetate polymer, a drug, and at least one clay, wherein the resulting composition comprises an adhesiveness increasing amount of clay, said amount of clay being from about 0.1 to about 20% by weight of said resulting composition, wherein the clay is a natural or synthetic clay selected from the group consisting of hydrated aluminum silicate, kaolinite, montmorillonite, atapulgite, illite, bentonite, and halloysite.

2. The method of claim 1, in which the drug comprises less than about 10% by weight of the composition.

3. The method of claim 1, in which the drug comprises less than about 5% by weight of the composition.

4. The method of claim 1, in which the clay is bentonite.

5. The method of claim 1, in which the clay is present in an amount of about 0.1 to about 6% by weight of the composition.

6. The method of claim 5, in which the drug is a steroid and the clay is present in an amount of about 0.1 to about 3% by the weight of the composition.

7. The method of claim 1, in which the drug is 17-$\beta$-estradiol.

8. The method of claim 1, in which the ratio of the multipolymer to the rubber is from about 1:5 to about 20:1.

9. The method of claim 8, in which the ratio of multipolymer to rubber is about 1:2 to about 15:1.

10. The method of claim 9, in which the drug is an estrogen, the ratio of multipolymer to rubber is about 3:1, and the amount of clay is about 0.1% to about 3%.

11. A dermal composition comprising an admixture of a drug, a pressure sensitive adhesive composition comprising a natural or synthetic rubber, and a multipolymer comprising a ethylene/vinyl acetate polymer and an acrylic polymer, in which the ratio by weight of the ethylene/vinyl acetate polymer to the acrylic polymer is about 1:20 to about 20:1, and the ratio by weight of the multipolymer to the rubber is about 1:10 to about 30:1, and further comprising from about 0.1 to about 20% by weight of an adhesiveness increasing amount of at least one natural or synthetic clay selected from the group consisting of hydrated aluminum silicate, kaolinite, montmorillonite, atapulgite, illite, bentonite, and halloysite.

12. The composition of claim 11, in which the clay is bentonite.

13. The composition of claim 11, which comprises at least one liquid solvent for one or more of the components of the composition.

14. The composition of claim 11, which comprises as approximate percent by weight, about 0.5 to about 50% of the drug, about 0.5 to about 20% of clay and about 0.5 to about 20% of the solvent.

15. The composition of claim 13, in which the solvent comprises a glycol.

16. The composition of claim 11 in which the clay is present in an amount of about 0.1 to about 6% by weight of the composition.

17. The composition of claim 16, in which the clay is present in an amount of about 0.1 to about 3% by weight of the composition.

18. The composition of claim 11, in which the drug is a steroid.

19. The composition of claim 19, in which the steroid is 17 $\beta$-estradiol and the clay is bentonite.

20. The composition of claim 19, in which the bentonite is present in an amount of from about 0.1% to about 3%.

21. The composition of claim 15 in which the glycol is selected from the group consisting of propylene and butylene glycols.

22. The composition of claim 11, in which the multipolymer to rubber ratio is from about 1:5 to about 20:1.

23. The composition of claim 22, in which the ratio of multipolymer to rubber is from about 1:2 to 15:1.

24. The composition of claim 23, in which the drug is an estrogen, the ratio of multipolymer to rubber is about 3:1, and the amount of clay is about 0.1% to about 3%.

25. The composition of claim 11, in the form of a shaped article having two opposed faces, a backing on one face, and a release liner on the other.

26. The composition of claim 11, further comprising a backing layer.

27. The composition of claim 11, further comprising a release liner.

28. The composition of claim 11, which is a multiphase system.

29. The composition of claim 11, comprising a first phase containing a first polymer and a second phase containing a second polymer.

30. The composition of claim 27, wherein the first polymer interpenetrates into the second polymer.

31. The composition of claim 11, further comprising a tackifying agent.

32. The composition of claim 11, wherein said ethylene-vinyl acetate polymer comprises between about 4 to 50% by weight of vinyl acetate.

33. The composition of claim 11, wherein the rubber comprises a polyisobutylene.

34. The composition of claim 11, wherein the acrylic polymer contains at least 50% by weight of acrylate or alklyacrylates monomeric units.

35. A method of producing the composition as claimed in claim 11, comprising the steps of mixing the components together in the presence of a solvent, coating the mixture onto a release liner, and removing an lower molecular weight solvents.

36. A method as claimed in claim 33, further comprising the step of joining a backing layer to the mixture.

* * * * *